US012564372B2

(12) United States Patent
Egorov

(10) Patent No.: US 12,564,372 B2
(45) Date of Patent: Mar. 3, 2026

(54) TACTILE ULTRASOUND METHOD AND PROBE FOR PREDICTING PRETERM BIRTH

(71) Applicant: Vladimir Egorov, Princeton, NJ (US)

(72) Inventor: Vladimir Egorov, Princeton, NJ (US)

( * ) Notice: Subject to any disclaimer, the term of this patent is extended or adjusted under 35 U.S.C. 154(b) by 19 days.

(21) Appl. No.: 18/144,752

(22) Filed: May 8, 2023

(65) Prior Publication Data

US 2023/0270403 A1 Aug. 31, 2023

Related U.S. Application Data

(63) Continuation-in-part of application No. 16/574,270, filed on Sep. 18, 2019, now abandoned.

(51) Int. Cl.
A61B 8/08 (2006.01)
A61B 8/00 (2006.01)
A61B 8/12 (2006.01)
B06B 1/06 (2006.01)

(52) U.S. Cl.
CPC .............. A61B 8/0866 (2013.01); A61B 8/12 (2013.01); A61B 8/485 (2013.01); A61B 8/54 (2013.01); B06B 1/067 (2013.01); B06B 2201/76 (2013.01)

(58) Field of Classification Search
None
See application file for complete search history.

(56) References Cited

U.S. PATENT DOCUMENTS

2004/0210136 A1* 10/2004 Varghese ............... A61B 8/445
600/443
2020/0022674 A1* 1/2020 Egorov ................ A61B 8/4494
2022/0087595 A1* 3/2022 Egorov ................ A61B 5/4337

* cited by examiner

*Primary Examiner* — Shahdeep Mohammed
(74) *Attorney, Agent, or Firm* — Boris Leschinsky

(57) ABSTRACT

A cervical probe, outfitted with a tactile sensor array and an ultrasound transducer, is designed for simultaneous collection of stress and ultrasound strain data from the same cervical sector. The gathered stress and strain data from multiple cervical sectors are sent to a data processor, which calculates cervical elasticity as a strain-to-stress ratio. Subsequently, an average stress-to-strain ratio is compared to a predetermined cutoff value to predict preterm birth at 24-28 gestational weeks.

11 Claims, 10 Drawing Sheets

101    102    103    104    105

106    107    108    109    110

200

201  202

203  204  205

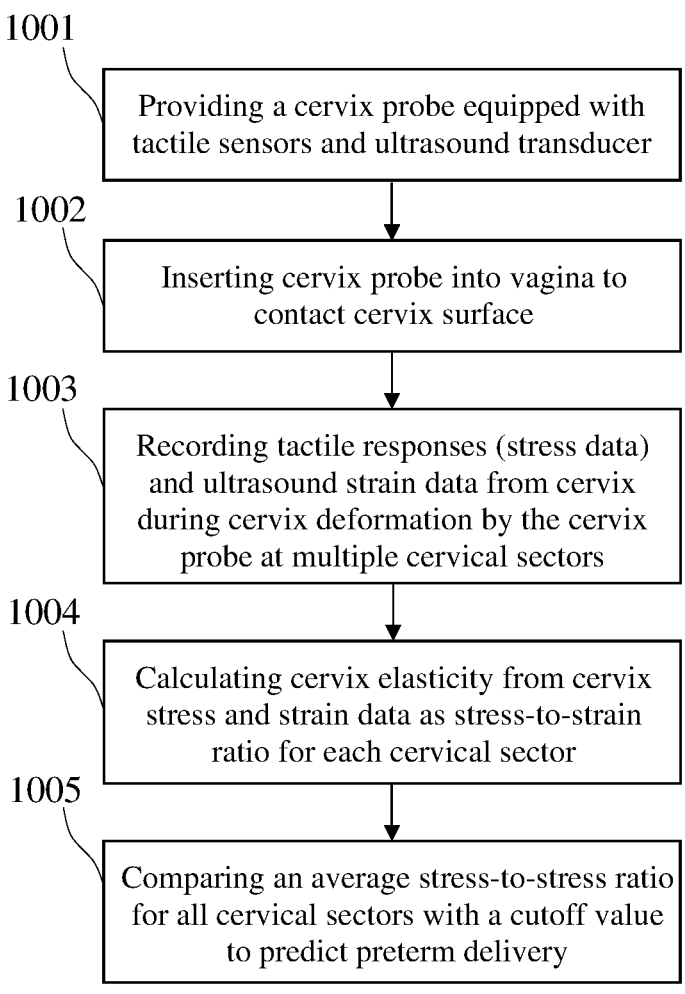

1001 Providing a cervix probe equipped with tactile sensors and ultrasound transducer 1002 Inserting cervix probe into vagina to contact cervix surface 1003 Recording tactile responses (stress data) and ultrasound strain data from cervix during cervix deformation by the cervix probe at multiple cervical sectors 1004 Calculating cervix elasticity from cervix stress and strain data as stress-to-strain ratio for each cervical sector 1005 Comparing an average stress-to-stress ratio for all cervical sectors with a cutoff value to predict preterm delivery

FIG. 10

TACTILE ULTRASOUND METHOD AND PROBE FOR PREDICTING PRETERM BIRTH

CROSS-REFERENCE DATA

This US Patent Application is a continuation-in part of a co-pending U.S. patent application Ser. No. 16/574,270 filed 18 Sep. 2019 by the same inventor and entitled METHOD AND PROBE FOR PREDICTING SPONTANEOUS PRE-TERM DELIVERY, which in turn is a continuation in part of a co-pending U.S. patent application Ser. No. 15/249,672 filed 29 Aug. 2016 by the same inventor and entitled METHODS AND PROBES FOR VAGINAL TACTILE AND ULTRASOUND IMAGING, which in turn claims a priority benefit from a U.S. Provisional Patent Application No. 62/215,227 filed 8 Sep. 2015 with the same title. All cited patent documents are incorporated herein in their respective entireties by reference.

GOVERNMENT-SUPPORTED RESEARCH

This invention was made with the US Government support under grant No. HD090793 awarded by Eunice Kennedy Shriver National Institute of Child Health & Human Development, USA. The Government has certain rights in this invention.

FIELD OF THE INVENTION

The present invention generally relates to cervix characterization of pregnant women. Specifically, the invention describes methods and devices for detecting conditions leading to spontaneous preterm delivery.

BACKGROUND

Preterm birth is a leading global cause of neonatal mortality despite intensive research and numerous advances in perinatal medicine. Almost 1 million children die each year due to complications of preterm birth. In almost all countries that have reliable data, preterm birth rates are increasing. Of the 14 million survivors per year, many face a lifetime of disability, including learning disabilities, visual and hearing impairments. The morbidities include respiratory distress syndrome, bronchopulmonary dysplasia, intraventricular hemorrhage, periventricular leukomalacia, necrotizing enterocolitis, sepsis, and retinopathy of prematurity. Long-term complications include cognitive disorders, behavioral problems, and cerebral palsy. These consequences imply devastating financial, social, and emotional effects on the parents or the affected children.

In 2021, preterm birth affected about 1 of every 10 infants born in the United States. The preterm birth rate rose 4% in 2021, from 10.1% in 2020 to 10.5% in 2021, according to the data collected by the Centers for Disease Control and Prevention.

A preterm birth is defined by the World Health Organization as a birth before 37 completed weeks of gestation or fewer than 259 days since the first day of a woman's last menstrual period. Preterm births occur for a variety of reasons. Most preterm births happen spontaneously. Common causes of a preterm birth (PTB) include multiple pregnancies, infections, chronic conditions, lifestyle, family history, and cervical incompetence. However, often no single cause is identified. Although PTB is often a multifactorial event, precocious cervical softening, shortening, and dilatation are a common denominator.

Clinical risk factors for PTB include obstetric history (familial genetic predisposition, uterine malformation, previous preterm labor, previous cervical surgery) and other aspects of the current pregnancy (multifetal gestation, genital tract bleeding and/or infection, fetal malformation, preterm rupture of membranes, shortened cervix, and other pregnancy complications including preeclampsia and gestational diabetes mellitus). A previous preterm birth before 34 weeks gestation is one of the strongest risk factors for subsequent preterm birth. However, insofar as nulliparous women have no past obstetric history to call upon, any such previous history risk factor-based assessment is not applicable in their situation. The PTB risk factors assessment alone is unreliable.

Extensive cervical remodeling is needed for the cervix to dilate and pass a fetus fully. While human parturition is not completely understood, it is a complex system that involves interactions between placental, fetal, and maternal mechanisms. The extracellular matrix of the cervix is primarily made up of tightly packed collagen bundles. Gradually, throughout the pregnancy, the composition of the cervix changes as the collagen density decreases, in addition to realignment and degradation of collagen cross-linking due to proteolytic enzymes, and an increase in the hyaluronic acid and water content. Further, through a cascade of events, inflammatory mediators increase the production of prostaglandins. Prostaglandins invading the cervix mediate the release of metalloproteases that further break down collagen and change the cervical structure. Cervical softening and distention result from these extracellular matrix compositional changes, specifically, increased vascularity and stromal and glandular hypertrophy, and are due, in part, to an increase in collagen solubility closer to delivery.

The cervical elasticity assessment currently used in clinical practice is relying on a clinician's evaluation of the cervix as 'hard,' 'medium' or 'soft,' which is descriptive and subjective. Clinicians use terms such as 'softening.' 'shortening.' 'funneling,' and 'effacing' to describe the changes in the cervical conditions that occur during pregnancy. Elasticity (consistency) is a component of the Bishop score [Bishop EH. Pelvic scoring for elective induction. Obstetrics Gynecology 1964; 24:266-8] that also includes dilation, effacement, station, and position, and is used basically to predict the success of induction of labor. The highest possible total Bishop score is 13, and the lowest possible score is 0. A Bishop score of 8 or greater is favorable for induction, or the chance of a vaginal delivery with induction and is similar to spontaneous labor. The cervical score described by Houlton in 1982 [Houlton MCC. Marivate M. Philpott RH. Factors associated with preterm labour and changes in the cervix before labour in twin pregnancy. Br J Obstet Gynaecology 1982; 89:190-194.] places a greater emphasis on cervical length. However, digital cervical score and Bishop score as predictors of PTB demonstrated poor diagnostic accuracy.

The uterine cervix must provide structural integrity and mechanical resistance to ensure normal development of the fetus as the uterus expands to accommodate the fetus' growth. Preterm delivery is closely related to a premature cervical ripening. The scientific premise for the invention is that the elasticity of a cervix is a sensitive parameter characterizing the stage of cervical conditions (ripening). The risk of spontaneous preterm delivery is increased in women who are found to have a short cervix by vaginal ultrasonography during pregnancy. Therefore, assessment of the cervix by a device measuring cervical elasticity and cervical length may provide an adequate approach for identifying pregnant women at high risk of PTB.

The current invention discloses a new device, referred to as a Cervix Monitor (CM), for measuring cervical elasticity and length, and a method for detecting conditions leading to PTB. The discovery and implementation into the clinical practice of novel biomarkers that could reliably identify women who will subsequently deliver preterm may enable timely medical attention and targeted therapeutic treatments aimed at improving maternal and fetal outcomes. The expected clinical impact may be significant for the considerable financial burden that it might reduce, not just for the health care system in the short term, but for the long-term care for the individual, the family, and the society.

SUMMARY

The present invention aims to address the limitations of existing technology by introducing a novel device and method for the objective biomechanical characterization of the cervix in pregnant women, as well as the detection of conditions that may lead to preterm birth. The Cervix Monitor (CM) is designed to measure stress applied to the external cervical surface using a tactile sensor array with pressure sensors, while also measuring the time-of-flight of an ultrasound pulse to the internal cervical surface with an ultrasound transducer in order to obtain strain data. The tactile and ultrasound sensors are situated at the head of the CM probe. The combined stress and strain data enable the calculation of cervix elasticity and effacement (length). The CM probe can be connected to a portable data processing unit, ensuring easy transportation of the entire system and 24/7 readiness for cervical monitoring in clinical settings.

Another object of the invention is to provide a novel method and device for objective characterization and real-time visualization of biomechanical properties of a cervix in two cervical sectors-anterior and posterior.

In embodiments, a method for predicting preterm delivery may include the steps of:

a) providing a cervix probe equipped with a plurality of tactile sensors and an ultrasound transducer positioned adjacent thereto,
 b) inserting the cervix probe into a vagina along a vaginal canal to contact a cervix surface of a pregnant woman,
 c) simultaneously acquiring cervix stress data with the tactile sensors and cervix strain data with the ultrasound transducer for the same sector of cervix surface during cervical tissue deformations by the cervix probe,
 d) calculating cervix elasticity and cervix length from the cervix stress data and cervix strain data, and
 e) predicting preterm delivery with the use of the cervical elasticity calculated as the strain-to-stress ratio below a predetermined cutoff value.

Additional method steps may include a series of repeated evaluations of the cervix status of a pregnant woman beginning from about 24 weeks of pregnancy, measurement of several (such as four) radially-oriented cervix sectors (upper, lower, left, and right), calculating cervix length from ultrasound pulse time-of-flight to an internal surface of the cervix, calculating cervix elasticity based on a finite element model or another computer simulation for cervix, comprising a cervix map with a set of predefined sectors each characterizing a respective measure of cervix elasticity and length data in this sector, as well as comprising a predictive model derived from a clinical validation study.

A novel probe for predicting preterm birth may include:

a front head equipped with a front-facing plurality of tactile sensors,
 the head being suitably shaped for contacting a cervix surface perpendicular to the internal surface of the cervix,
 the plurality of tactile sensors forming together a tactile sensor array located over at least some of the front-facing head surface of the probe,
 an ultrasound transducer located adjacent to or in the center of the plurality of tactile sensors on the same front-facing surface of the probe head,
 wherein the tactile sensor array is configured to acquire stress signals, and the ultrasound transducer is configured to emit an ultrasound pulse and to acquire a scattered ultrasound waveform from soft tissues of the cervix for the same sector of the cervix,
 a control unit operably connected to the tactile sensors and the ultrasound transducer and configured for acquiring the stress data from tactile sensors and the scattered ultrasound waveform from the ultrasound transducer, and
 a data processor operably connected to the control unit and configured for calculating cervical elasticity and length from stress and strain data, and predicting preterm birth based on the strain-to-stress ratio below the cutoff value.

In embodiments, a cervix-facing surface of the probe head may include a durable elastic medical-grade silicone layer to allow for stress transmission via reversible deformation thereof from the cervix-facing surface to pressure sensors located underneath. This allows for multiple disinfections of the probe. The ultrasound transducer may be made using a piezoceramic composite material with a mylar film as an acoustic matching layer between an ultrasound transducer and front-facing surface, and a silicone backing layer behind the ultrasound transducer.

BRIEF DESCRIPTION OF DRAWINGS

Subject matter is particularly pointed out and distinctly claimed in the concluding portion of the specification. The foregoing and other features of the present disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

FIG. 10 presents a block diagram of the steps of the method for predicting preterm delivery.

DETAILED DESCRIPTION OF THE INVENTION

Figure 1:
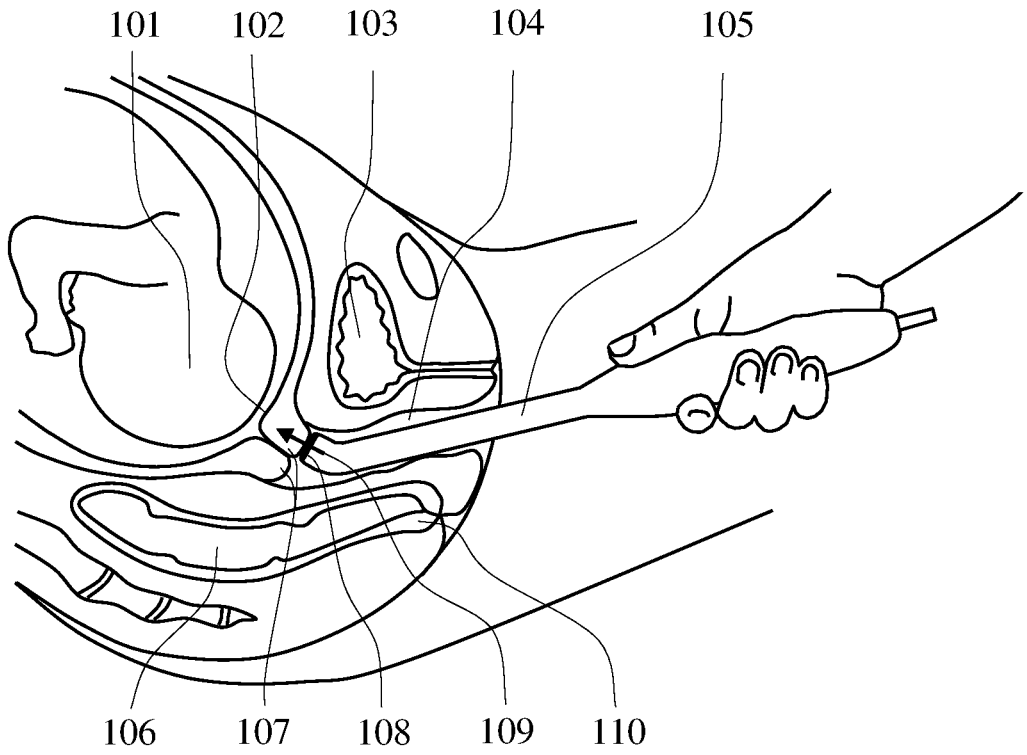
FIG. 1 illustrates a cervix probe location during the acquisition of stress and ultrasound strain data from the cervix using cervical deformation along the black arrow.

The following description sets forth various examples along with specific details to provide a thorough understanding of claimed subject matter. It will be understood by those skilled in the art, however, that claimed subject matter may be practiced without one or more of the specific details disclosed herein. Further, in some circumstances, well-known methods, procedures, systems, components and/or circuits have not been described in detail in order to avoid unnecessarily obscuring claimed subject matter. In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the figures, can be arranged, substituted, combined, and designed in a wide variety of different configurations, all of which are explicitly contemplated and make part of this disclosure.

Specific terms are used in the following description, which are defined as follows:

"tactile sensor" is the sensor capable of measuring an applied force averaged per sensor area or pressure;

"ultrasound transducer" is the sensor capable to emit and receive an acoustic wave;

"stress" is a force per unit of area (pressure) measured at the surface of the cervix;

"strain" is a soft tissue displacement under tissue deformation;

"preterm delivery" is a synonym to "preterm birth"

FIG. 1 illustrates a cervix probe 105 location during acquisition of stress and strain data from a cervix 107 at cervix deformation with the probe head 108 oriented along arrow 109. Shown in FIG. 1 is a sagittal cross-section of the pelvic floor of a pregnant woman with a fetus 101. The pelvic landmarks are a bladder 103, a vagina 104, and a rectal canal 106 with an anus 110. The probe head 108 may have a flat surface with tactile sensors and ultrasound transducers contacting the cervix 107 surface, either directly or through an elastic protective layer. The probe head 108 may be designed to have sensors in contact with the entire cervix or individual parts thereof. In other embodiments, the head 108 may include groups of sensors designed to contact individual sectors of cervix 107; such as 2 sectors, 3 sectors, 4 sectors, 5 sectors, 6 sectors, 7 sectors, 8 sectors, 9 sectors, 10 sectors, or more, as the invention is not limited in this regard. The following description uses a two-sector exemplary approach for the characterization of the cervix, namely an upper or anterior sector, and a lower or posterior sector.

FIG. 1 further shows the probe head 108 placed in contact with the anterior cervical sector. The size of the head 108 and the location of the sensors may be arranged for the head to be used to characterize the entire cervix all at once, or alternatively for characterizing each desired sector or groups of adjacent sectors of the cervix at a time.

A front portion of probe head 108 containing sensors may be suitably shaped for contacting the cervix surface generally perpendicular to the internal surface 102 of the cervix 107. It allows the acquisition of ultrasound-reflected signal from the internal surface 102 and measuring a time-of-flight for the ultrasound-reflected signal. Taking into account the acoustic speed of about 1,540 m/s for soft human tissues, one may calculate the cervix length from the internal surface to the cervix surface contacting the probe head 108. Changes in the time-of-flight during the cervix compression or deformation by the probe head 108 may be used to provide strain data for the respective cervix sector or a group of sectors which are under investigation. A plurality of tactile sensors (from 1 to 16 sensors) may be used to form together a tactile array located over at least a portion of the probe head 108, which may be configured to record stress data from the cervix surface during cervical tissue deformation by the front portion of the probe 105. The tactile sensor array may include 1, 2, 3, 4, 5, 6, 7, 8, 9, 10, 11, 12, 13, 14, 15, or 16 suitable tactile sensors, as the invention is not limited in this regard.

An ultrasound transducer may be located adjacent to the plurality of tactile sensors over the same front portion of the probe head 108. The tactile sensor array may be configured to acquire stress data in the form of pressure data on each tactile sensor, while the ultrasound transducer may be configured to first emit an ultrasound pulse and then to acquire a scattered ultrasound waveform from soft tissues of the cervix including the internal surface for the same sector of the cervix. A control unit (not shown) may be operably connected to the tactile sensors array and to the ultrasound transducer. The control unit may further be configured for acquiring stress data from tactile sensors and scattered ultrasound waveform data from the ultrasound transducer. A data processor (not shown) may be operably connected to the control unit and configured for calculating cervix elasticity and length from stress data and ultrasound waveforms.

Figure 2:
FIG. 2 shows an embodiment of a probe for predicting preterm delivery.

FIG. 2 presents an exemplary embodiment of a probe 200 for predicting preterm delivery. The probe 200 may comprise a handle 205, a shaft 204, and a head 203 with a flat surface configured for contacting the cervix, as shown in FIG. 1. The probe 200 may contain a tactile array 202 with a plurality of sensors (four in this case) and at least one ultrasound transducer 201 as shown in FIG. 2. In one embodiment, the ultrasound 5.0 MHz transducer 201 measuring about 3.5 mm in size may be configured for working in the pulse-echo mode with a data acquisition resolution of about 20 ns (50 MHz sample rate). Biocompatible, two-component silicone (such as, for example, made by NuSil Technology, CA) may be employed to provide sensor assembly with a functional, durable, and stable mechanical protection cover. A proprietary printed circuit board of a control unit may be designed to perform the dual functions of stress signal acquisition and generation/acquisition of synchronized ultrasound signals. Its key features are to operate and acquire data from the plurality of tactile sensors 202 and the ultrasound transducer 201 at about 100 data frames per second. The stress measurement noise level in this example is about 25 Pa within the operational range of 40 kPa. The ultrasound transmitting pulses have a peak amplitude below 50 V and a length of less than 1 μs, which provide acoustic power significantly below the limits established by the FDA for ultrasound emission in obstetrics: spatial-peak temporal-average $I_{spta}=13$ (mW/cm2), spatial-peak pulse-average intensity $I_{sppa}=86$ (W/cm2), and mechanical index MI=1.0.

Medical grade 316 stainless steel, used in the production of surgical instruments, may be used to fabricate the probe shaft 204, while biocompatible plastic materials may be used for probe handle 205 and a head 203. The device software interface may be configured to allow real-time observation of the cervical ultrasound signal as well as the level of applied stress. The ultrasound peak position for the cervix internal surface signal may be calculated with the use of a signal envelope after the Gaussian complex wavelet filtering at 5 MHz frequency. The cervical elasticity may be calculated as a stress-to-strain ratio of applied load to the cervix surface from the probe (stress) to the resultant changes in the cervical length (strain). This approach was validated with the soft tissue models in bench testing and verification. Young's modulus may be calculated from the stress-strain data based on a semi-infinitive linear elastic model and based on a finite element modeling of the cervix deformation with the probe 200.

The cervix examination procedure may comprise the following four main steps:

(1) inserting the speculum into a vagina to provide appropriate visualization and access to the cervix;

(2) performing probe measurements at various portions of the cervix, such as for example at 6 and 12 o'clock, specifying the probe head location on the cervix surface and on a cervix map displayed to the user;

(3) reviewing of the measurement results (ultrasound reflected waves and applied loads), and (4) removal of the probe and speculum from the vagina.

Figure 3:
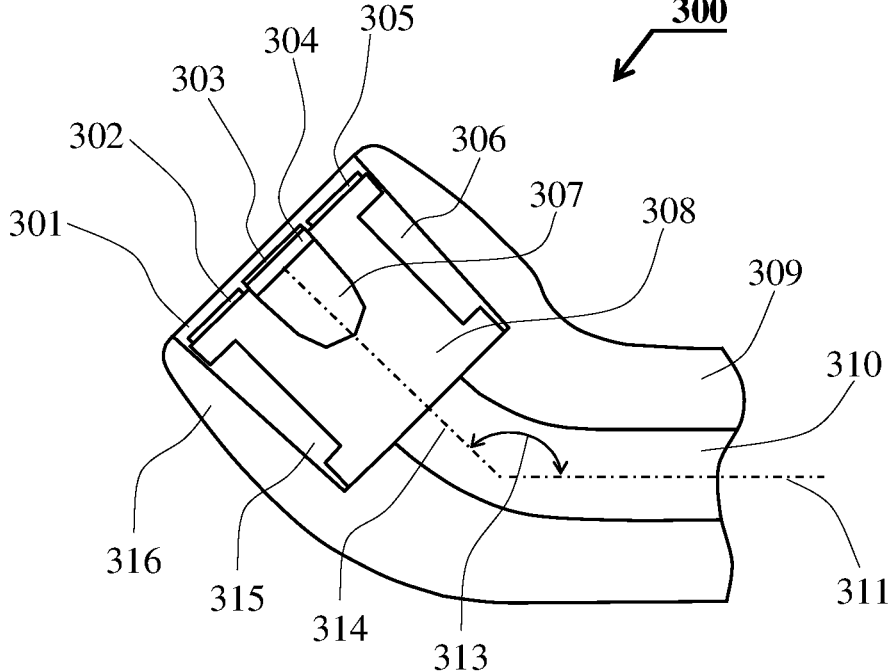
FIG. 3 shows a close-up cross-sectional view of a probe head with tactile and ultrasound transducers.

FIG. 3 presents an embodiment of a cervix probe with a head 300 equipped with tactile sensors 302 and 305 and an ultrasound transducer 304 for predicting preterm delivery. The number of tactile sensors may be more than 2, as mentioned above. All tactile sensors may be positioned around the ultrasound transducer 304, which may be placed in a geometrical center of the plurality of tactile sensors of the array. A tactile sensor may be made as a capacitive type sensor, although other force sensors may be used for the purposes of the invention.

The ultrasound transducer may be built from composite piezoceramic materials, for example, 1-3 composites, and may be characterized by lower acoustic impedances (for example ranging from about 5 MRayl to about 30 MRayl), high coupling coefficients (typically about 0.6 to about 0.75), high bandwidth and lower mechanical quality factor (Qm). The ultrasound transducer 304 may be covered with an acoustic matching layer 303 on the front side and a backing layer 307 on the backside. The matching layer 303 may be preferably made using a mylar film of 0.09 mm thickness for 5 MHz. The thickness of the matching layer 303 was optimized experimentally for other frequencies by maximizing scattered signal amplitude and minimizing signal length. The backing layer 307 may be filled by silicone with attenuation of about 20 dB/mm at 6 MHz in a cavity with a depth of about 5 mm located behind the ultrasound transducer 304. Both tactile sensors 302, 305, and the ultrasound transducer 304 may be positioned on a support base 308 placed inside the probe body 309 with a central cavity 310 extending therethrough for housing electrical wiring of the sensors and the transducer. After positioning the support base 308 with assembled sensors and transducer therein in the suitably sized front opening of the probe body 309, it may be secured therein by filling the spaces 301, 306 and 315 with a medical grade silicone having an acoustic impedance of about 1 MRayl. The thickness of a surface layer 301 covering the tactile sensors 302, 305 may be about 0.4 mm. The silicone layer 303 covering the ultrasound transducer 304 may be about 0.3 mm thick. The probe head 316 may have a diameter of about 10-14 mm. The angle 313 between the probe central line in shaft 311 and central line 314 inside the probe head may be about 140 degrees. This allows positioning of the probe head orthogonally to the cervix surface and, at the same time, allows for an easy insertion of the probe into a vagina and removal therefrom after the test procedure is complete.

Figure 4:
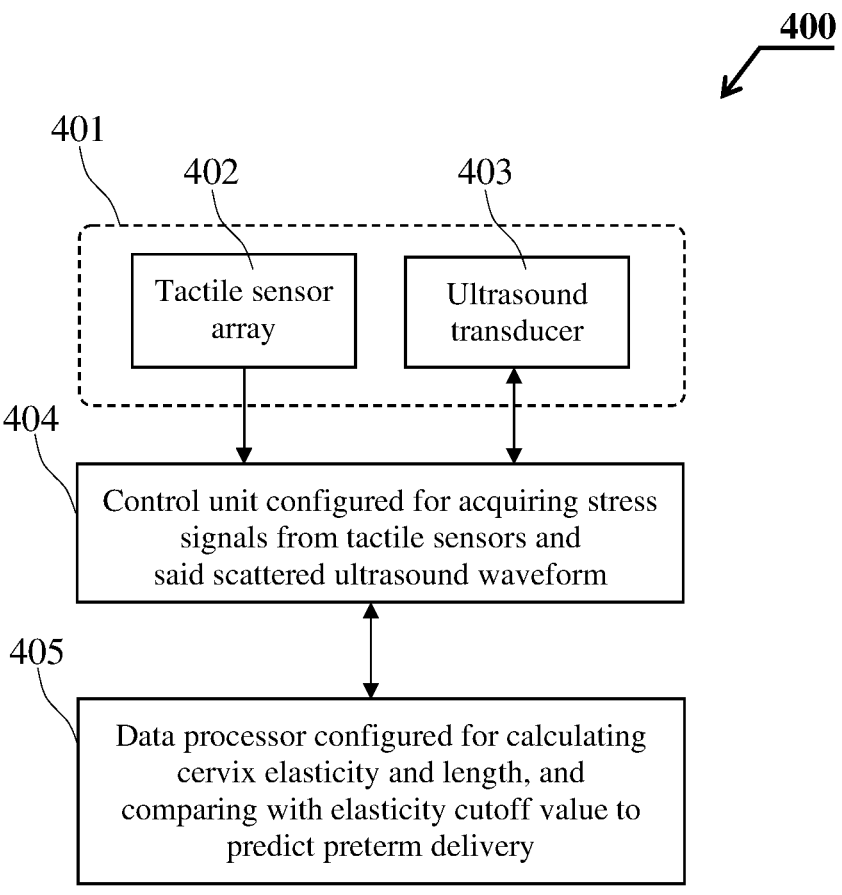
FIG. 4 presents a block diagram of the probe of the present invention.

FIG. 4 presents a block diagram of a system 400 for predicting preterm delivery. A probe 401 comprises a plurality of tactile sensors 402 forming together a tactile sensor array located over at least a portion of the probe head. Probe 401 further comprises an ultrasound transducer 403 located adjacent to the plurality of tactile sensors on the same front surface. The tactile array 402 may be configured to acquire stress data, and the ultrasound transducer 403 is configured to emit an ultrasound pulse and to acquire a scattered ultrasound waveform from soft tissues of the cervix for the same sector of the cervix. A control unit 404 may be operably connected to the tactile sensors 402 and the ultrasound transducer 403 and configured for acquiring the stress data from tactile sensors 402 and the scattered ultrasound waveform from the ultrasound transducer 403. A data processor 405 is operably connected to the control unit 404 and configured for calculating cervix elasticity and length from stress data and ultrasound waveforms, which in turn may be used for comparing the stress-to-strain ratio with a cutoff value to predict preterm delivery.

Figure 5:
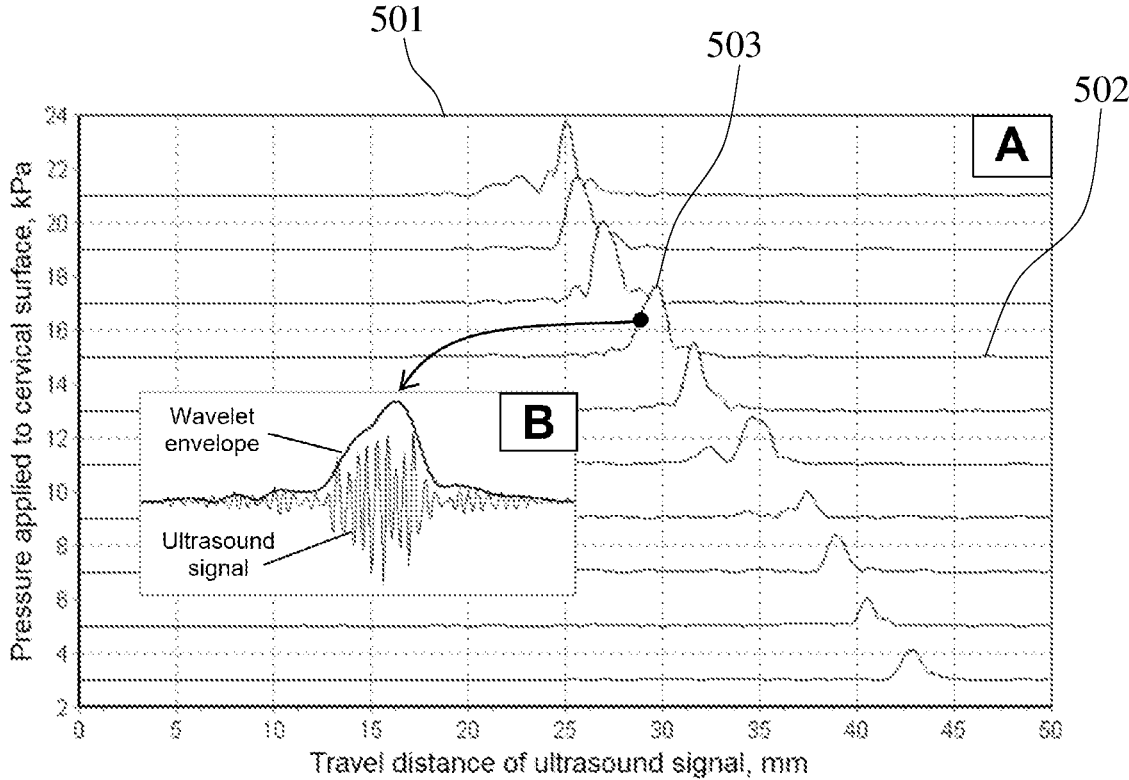
FIG. 5 shows a graph with ultrasound signals (envelopes) reflected from the internal cervical surface during cervix deformation by the probe.

FIG. 5 shows exemplary ultrasound signals 501 for a pregnant woman at the 25th gestational week obtained from cervical tissue during cervix deformation by the probe (see panel A); one of these signals is denoted as 502. The recorded ultrasound signals have an identifiable amplitude peak 503 reflected from the cervical internal surface, which may be used for measurement of ultrasound time-of-flight and cervix length in millimeters (mm) as shown along the horizontal axis. The peak position was calculated with the use of signal envelope lines (Gaussian complex wavelet filtering) as shown in the B-panel of FIG. 5. At the cervical compression, said peak 503 is shifted left, demonstrating the dependence of applied stress to the cervix (see left vertical axis) from the cervix length calculated from the travel distance during cervical deformation (see horizontal axis). The availability of stress-to-strain data allows the calculation of the cervix elasticity.

Examples

Figure 6:
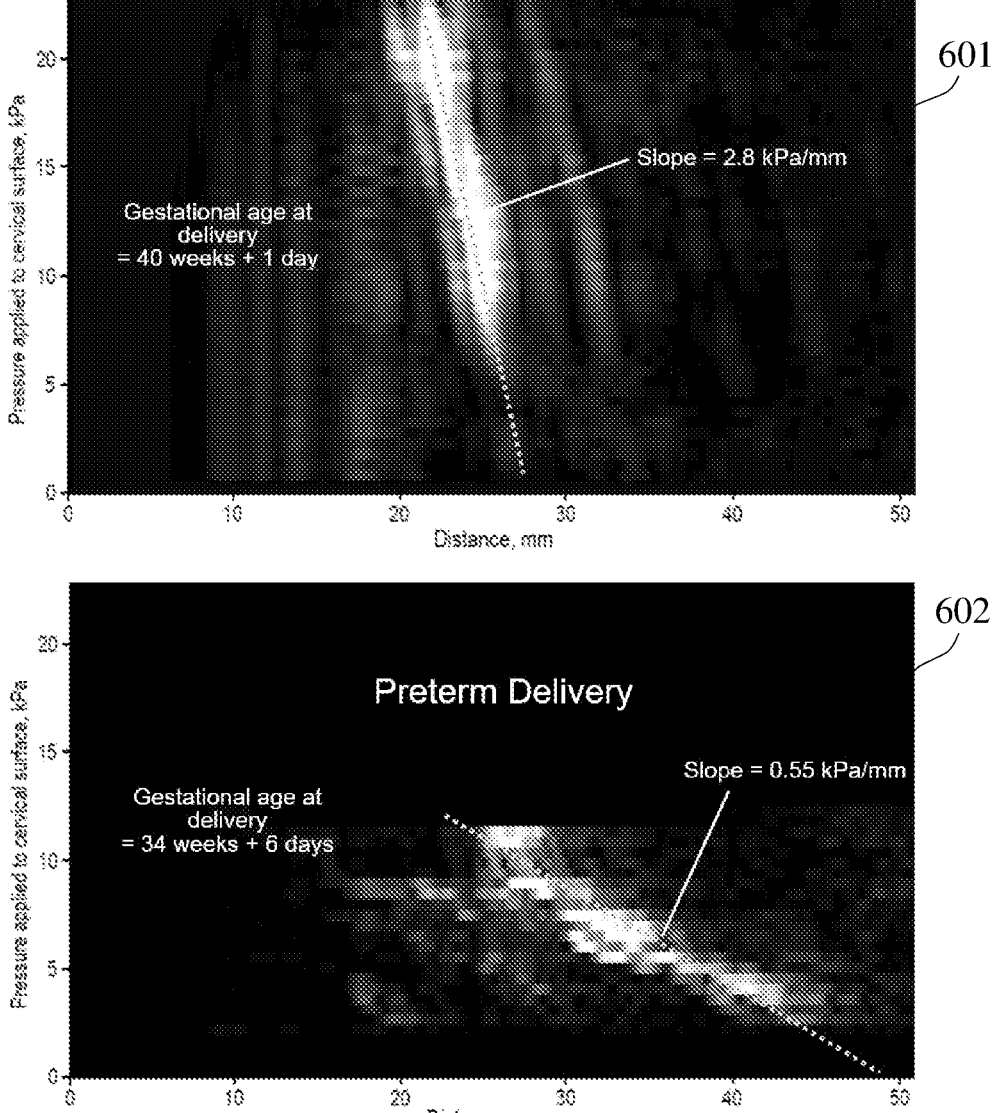
FIG. 6 presents stress-strain cervical mapping with ultrasound signals reflected from the internal cervical surface and applied pressure at the cervix by the CM probe acquired at 24-28 gestational weeks.

FIG. 6 shows the clinical results of the measured cervical stress-to-strain ratio for two pregnant women acquired at 24-28 gestational weeks with the CM probe. Specifically, panel 601 shows the results for a woman who delivered at 40 weeks and 1 day (term birth); the slope of the stress-to-strain ratio (see dotted line) calculated as described in FIG. 5 was 2.8 kPa/mm. Panel 602 shows the results for a woman who delivered at 34 weeks and 6 days (preterm birth); the slope of the stress-to-strain ratio was 0.55 kPa/mm at 25 gestational weeks. In these cases, the average stress-to-strain ratio for anterior and posterior cervical compartments was calculated and taken into account.

Figure 7:
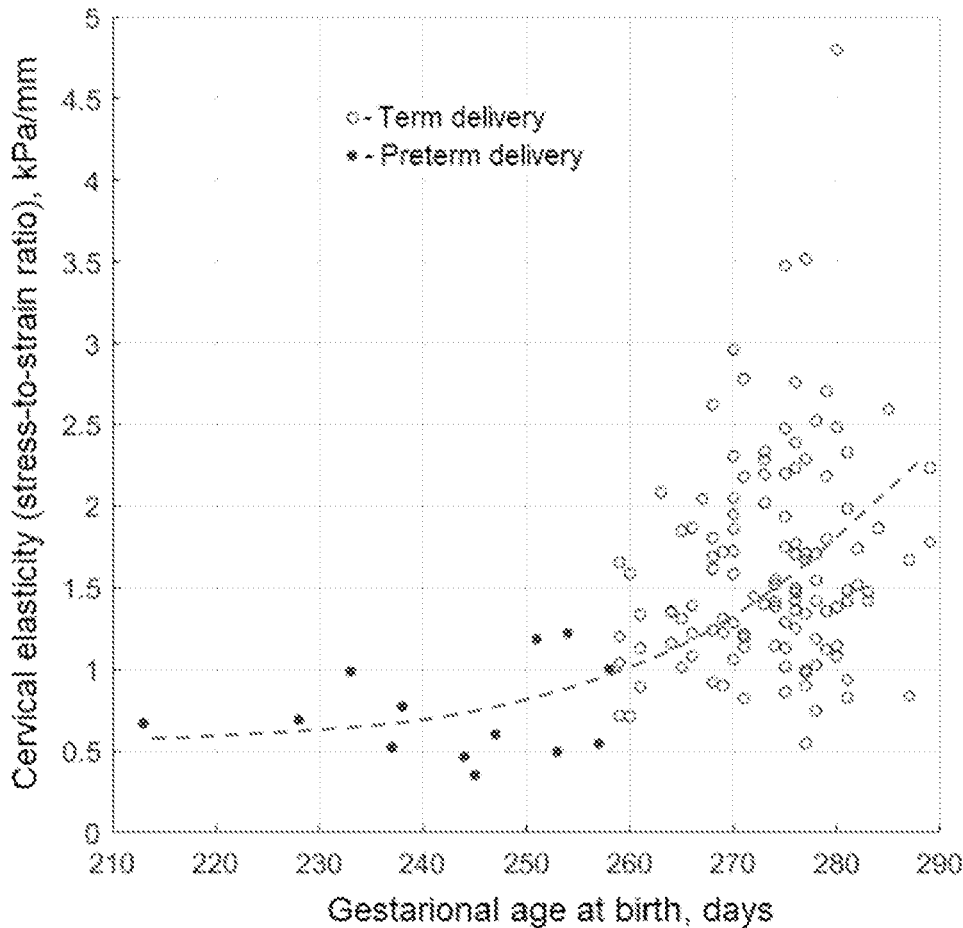
FIG. 7 presents cervical elasticity calculated as a stress-to-strain ratio for 129 pregnant women at 24-28 gestational weeks versus the gestational age at birth. Preterm delivery is presented by filled circles.

FIG. 7 shows cervical elasticity measured by the CM as stress-to-strain ratio for 129 pregnant women at 24-28 gestational weeks versus the gestational age at birth. Preterm delivery is presented by filled circles. The dashed line demonstrates a tendency for the cervical elasticity decrease versus the gestational age at birth.

Figure 8:
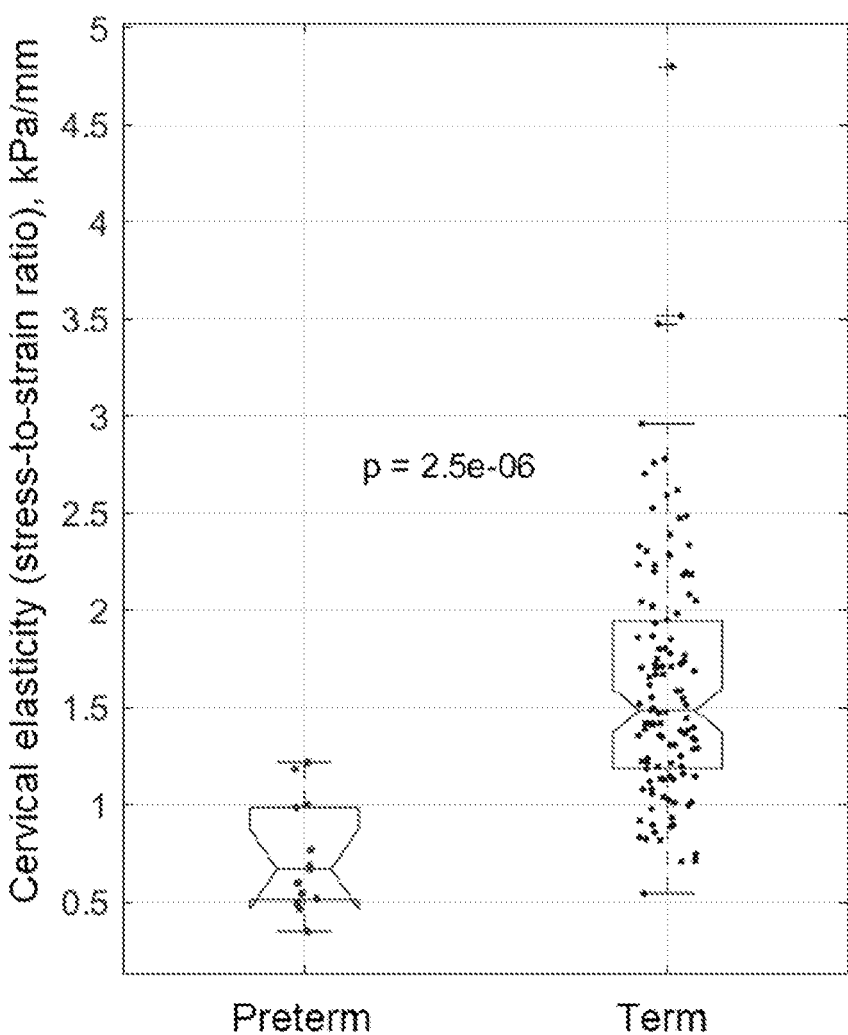
FIG. 8 presents boxplots for CM examination data acquired at 24-28 gestational weeks. Preterm group is in the left and term group is on the right boxplot.

FIG. 8 presents boxplots for CM examination data acquired at 24-28 gestational weeks. Preterm group is on the left, and the term group is on the right boxplot. A significant difference is observed between these groups, with elasticity decrease in the preterm group with t-test $p=2.5\times10^{-6}$ between these groups.

Figure 9:
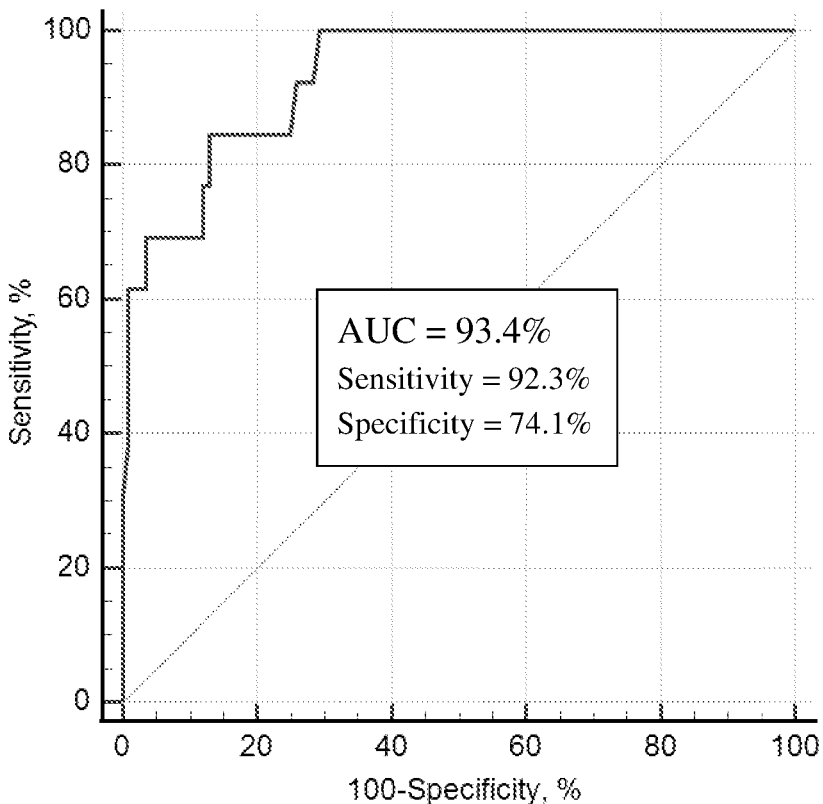
FIG. 9 presents receiver operating characteristic (ROC) curve for prediction of the preterm delivery (<37 weeks) resulting from cervical elasticity data acquired at 24-28 gestational weeks with the CM.

FIG. 9 presents receiver operating characteristic (ROC) curve for the prediction of the preterm delivery (<37 weeks) resulting from cervical elasticity data acquired at 24-28 gestational weeks with the CM. Receiver operating characteristic (ROC) analysis revealed that cervical elasticity had a sensitivity of 92.3% (95% CI, 64.0-98.18) and a specificity of 74.1% (95% CI, 65.28-81.8) for predicting PTB at a cutoff value of 1.22 kPa/mm for the cervical stress-to-strain ratio. The area under the ROC curve was 93.4% (95% CI, 87.6-97.0) for predicting PTB based solely on cervical elasticity data (stress-to-strain ratio).

FIG. 10 presents a block diagram of a method for predicting preterm birth, comprising:

step 1001 of providing a cervix probe equipped with a plurality of tactile sensors and an ultrasound transducer positioned adjacent thereto, step 1002 of inserting the cervix probe into a vagina along a vaginal canal to contact the cervix surface of a pregnant woman, step 1003 of simultaneously recording/acquiring cervix stress data using the tactile sensors and ultrasound cervix strain data for the same sector of the cervix during cervical tissue deformations by the cervix probe; this step is repeated for multiple cervical sectors, step 1004 of calculating cervix elasticity and length from the cervix stress and strain data for each contacted cervical sector, and step 1005 of comparing an average stress-to-strain ratio for all contacted cervical sectors with the cutoff value of 1.22 kPa/mm.

Additional method steps may include conducting this evaluation multiple times for a pregnant woman beginning from 24 weeks of pregnancy, measurement from four (4) cervix sectors (upper, lower, and lateral right and left), calculating cervix length from ultrasound pulse time-of-flight to the internal cervical surface, calculating cervix elasticity based on a finite element model simulation for cervix, composing a cervix map with a set of sectors with cervix elasticity and length data per every sector, and comprising a predictive model derived from a clinical study.

Although the invention herein has been described with respect to particular embodiments, it is understood that these embodiments are merely illustrative of the principles and applications of the present invention. It is, therefore, to be understood that numerous modifications may be made to the illustrative embodiments and that other arrangements may be devised without departing from the spirit and scope of the present invention as defined by the appended claims.

What is claimed is:

1. A method for predicting preterm delivery, the method comprising the steps of:

a) providing a cervix probe with a head equipped with a plurality of tactile sensors and an ultrasound transducer, said head positioned at an angle to a probe shaft, thereby said probe is configured for an orthogonal contact with a cervix surface of a subject, b) inserting said cervix probe into a vagina to contact said cervix surface, c) using said cervix probe to deform said cervix surface while simultaneously acquiring cervix stress data via said tactile sensors and cervix strain data via said ultrasound transducer from same sector of a cervix, d) calculating cervix elasticity as a strain-to-stress ratio and cervix length using said cervix stress data and said cervix strain data, and e) comparing the stress-to-strain ratio with a predetermined fixed numerical cutoff value of stress-to-strain ratio of at least 1.22 kPa/mm, which is defined prior to examination of step (b) to predict preterm birth, wherein said steps (b) through (e) are performed on a pregnant woman at 24-28 weeks of pregnancy.

2. The method for predicting preterm delivery, as in claim 1, wherein in step (e) the predetermined fixed numerical cutoff value of stress-to-strain ratio is derived from receiver-operating-characteristic (ROC) analysis of a clinical validation study.

3. The method for predicting preterm delivery, as in claim 1, wherein said steps (c) and (d) are conducted for more than one cervical sector of said cervix surface, and an average stress-to-strain ratio is calculated for all contacted cervical sectors.

4. The method for predicting preterm delivery, as in claim 1, wherein said step (d) further comprising a step of calculating cervix length from ultrasound pulse time-of-flight from said cervix surface to an internal surface of the cervix.

5. The method for predicting preterm delivery, as in claim 1, wherein in step (e), the predetermined fixed numerical cutoff value of stress-to-strain ratio was established in a prospective clinical validation study.

6. The method for predicting preterm delivery, as in claim 3, wherein said steps (c) and (d) are performed on at least two cervical sectors of said cervix surface.

7. The method for predicting preterm delivery, as in claim 6, wherein said at least two cervical sectors are an anterior cervical sector and a posterior cervical sector.

8. A probe for predicting preterm delivery, said probe comprising:

a head equipped with a plurality of front-facing tactile sensors and a front-facing ultrasound transducer, said head is positioned at an angle to a probe shaft, thereby said probe is configured for an orthogonal contact with a cervix surface, said plurality of tactile sensors forming together a pressure sensor array configured to acquire stress data and located over at least a portion of said head, said ultrasound transducer is positioned adjacent to said plurality of tactile sensors on said head, the ultrasound transducer is configured to emit an ultrasound pulse and to acquire a scattered ultrasound waveform from said cervix surface during cervix deformation by said probe, wherein the stress data and the scattered ultrasound waveform are from same sector of a cervix, a control unit operably connected to said pressure sensory array for acquiring said stress data and said ultrasound transducer for acquiring said scattered ultrasound waveform, and a data processor operably connected to said control unit and configured for calculating cervix elasticity and cervix length using said stress data and said ultrasound waveforms, said data processor is further configured to compare cervical elasticity calculated as a strain-tostress ratio to a predetermined fixed numerical cutoff value of stress-to-strain ratio of at least 1.22 kPa/mm, which is defined prior to examination to predict preterm birth.

9. The probe, as in claim 8, wherein said head further comprises an elastic layer covering said pressure sensory array and said ultrasound transducer to allow reversible stress transmission therethrough and multiple disinfections of said probe.

10. The probe, as in claim 8, wherein said ultrasound transducer is made using a piezoceramic composite material with a mylar film with a predetermined thickness as an acoustic matching layer.

11. The probe, as in claim 8, wherein said ultrasound transducer has an elastic backing layer to allow attenuation of acoustic backscattering from a support base housing thereof.

* * * * *